United States Patent
Ohtake et al.

(10) Patent No.: US 9,683,211 B2
(45) Date of Patent: *Jun. 20, 2017

(54) METHOD OF PROMOTING GROWTH OF GREEN ALGAE

(71) Applicant: SHOWA DENKO K.K., Tokyo (JP)

(72) Inventors: Noriko Ohtake, Kawasaki (JP); Tadashi Yoneda, Kawasaki (JP)

(73) Assignee: SHOWA DENKO K.K., Minato-ku, Tokyo (JP)

(*) Notice: Subject to any disclaimer, the term of this patent is extended or adjusted under 35 U.S.C. 154(b) by 34 days.

This patent is subject to a terminal disclaimer.

(21) Appl. No.: 14/399,587

(22) PCT Filed: Feb. 4, 2014

(86) PCT No.: PCT/JP2014/052531
§ 371 (c)(1),
(2) Date: Nov. 7, 2014

(87) PCT Pub. No.: WO2014/119794
PCT Pub. Date: Aug. 7, 2014

(65) Prior Publication Data
US 2015/0140642 A1  May 21, 2015

(30) Foreign Application Priority Data

Feb. 4, 2013  (JP) .................................. 2013-019975

(51) Int. Cl.
*C12N 1/12*    (2006.01)
*C12N 13/00*   (2006.01)
*C12P 23/00*   (2006.01)

(52) U.S. Cl.
CPC ............. *C12N 1/12* (2013.01); *C12N 13/00* (2013.01); *C12P 23/00* (2013.01)

(58) Field of Classification Search
CPC  C12N 1/12; C12N 13/00; C12P 23/00; A61K 2300/00; A61K 31/51; A61K 31/525; A61K 31/714; A61K 36/05; A61K 36/23; A61K 36/31; A61K 36/34; A61K 36/48; A61K 36/534; A61K 36/899; A61K 2039/505; A01N 25/34; A01N 27/00; A01N 29/02; A01N 33/18
See application file for complete search history.

(56) References Cited

U.S. PATENT DOCUMENTS

2011/0312062 A1  12/2011  Nordvik et al.

FOREIGN PATENT DOCUMENTS

| CN | 102766578 A * | 11/2012 |
| EP | 1443104 A1 | 8/2004 |
| EP | 2740349 A1 | 6/2014 |
| JP | 08-103167 A | 4/1996 |
| JP | 11-266727 A | 10/1999 |
| JP | 2004147641 A | 5/2004 |
| JP | 2007-097584 A | 4/2007 |
| JP | 2010-200746 A | 9/2010 |
| JP | 2012-179009 A | 9/2012 |
| JP | 2013-201903 A | 10/2013 |
| WO | 2013/021675 A1 | 2/2013 |

OTHER PUBLICATIONS

Weiqi Fu, et al., "Enhancement of carotenoid biosynthesis in the green microalga Dunaliella salina with light-emitting diodes and adaptive laboratory evolution", Applied Microbiology Biotechnology, 2013, pp. 2395-2403, vol. 97.
Tomohisa Katsuda, et al., "Astaxanthin production by Haematococcus pluvialis under illumination with LEDs", Enzyme and Microbial Technology, 2004, pp. 81-86, vol. 35.
H. Oldenhof, et al., "Blue Light Delays Commitment to Cell Division in Chlamydomonas reinhardtii", Plant Biol., 2004, pp. 689-695, vol. 6.
Tomohisa Katsuda, et al., "Effect of Flashing Light from Blue Light Emitting Diodes on Cell Growth and Astaxanthin Production of Haematococcus pluvialis", Journal of Bioscience and Bioengineering, 2006, pp. 442-446, vol. 102, No. 5.
International Search Report for PCT/JP2014/052531, dated Apr. 1, 2014.
Written Opinion for PCT/JP2014/052531, dated Apr. 1, 2014.
Kyong-Hee Park et al: "Optimization of algal photobioreactors using flashing lights", Biotechnology and Bioprocess Engineering, vol. 5, No. 3, 2000, pp. 186-190.
International Search Report dated Apr. 1, 2014 issued in counterpart International Application No. PCT/JP2014/052488.
International Search Report dated Apr. 1, 2014 issued in counterpart International Application No. PCT/JP2014/052515.
Written Opinion dated Apr. 1, 2014 issued in counterpart International Application No. PCT/JP2014/052515.
Notice of Allowance dated Oct. 28, 2014 from the Japanese Patent Office issued in corresponding Application No. 2014-530017.
Communication dated Apr. 13, 2016 from the United State Patent and Trademark Office issued in corresponding U.S. Appl. No. 14/405,680.
Communication dated Apr. 11, 2016 from the United States Patent and Trademark Office issued in corresponding U.S. Appl. No. 14/400,351.

(Continued)

Primary Examiner — Debbie K Ware
(74) Attorney, Agent, or Firm — Sughrue Mion, PLLC

(57) ABSTRACT

Provided is a method of culturing green algae which promotes the growth of the green algae which is in a state of being a green swarm cell by irradiating the green algae that accumulate astaxanthin with an artificial light. The green algae are grown in a liquid medium while maintaining a state in which the color of a culture solution of the green algae is green or brown by intermittently radiating a red illumination light while continuously radiating a blue illumination light.

9 Claims, No Drawings

(56) References Cited

OTHER PUBLICATIONS

Katsuda T. et al., "Effect of Light Intensity and Frequency of Flashing Light from Blue Light Emitting Diodes on Astaxanthin Production by Haematococcus pluvialis", Journal of Bioscience and Bioengineering, vol. 105, No. 3, pp. 216-220, 2008.
Ana Catarina Guedes et al., "Microalgae as Sources of Carotenoids", Marine Drugs, Apr. 20, 2011, vol. 9, pp. 625-644, ISSN 1660-3397.
Communication dated Jul. 14, 2016, issued by the European Patent Office in corresponding European Application No. 14745735.2.
Z-Hun Kim et al: "Red and Blue Photons Can Enhance the Production of Astaxanthin from Haematococcus pluviatis", Algae, vol. 24, No. 2, Jun. 2009 (Jun. 2009), pp. 121-127.
Kyong-Hee Park et al: "Optimization of algal photo bioreactors using flashing lights", Biotechnology and Bioprocess Engineering, vol. 5, No. 3, 2000, pp. 186-190.
Kyong-Hee Park et al: "Effect of flashing light on oxygen production rates in high-density algal cultures", Journal of Microbiology and Biotechnology, vol. 10, No. 6, 2000, pp. 817-822.
Kim Z H et al: "Enhanced production of astaxanthin by flashing light, using Haematococcus pluvialis", Enzyme and Microbial Technology, Stoneham, MA, US, vol. 39, No. 3, Jul. 3, 2006 (Jul. 3, 2006), pp. 414-419.
Lababpour A et al: "Fed-batch culture under illumination with blue light emitting diodes (LEDs) for astaxanthin production by Haematococcus pluvialis", Journal of Bioscience and Bioengineering, Elsevier, Amsterdam, NL, vol. 100, No. 3, Sep. 2005 (Sep. 2005), pp. 339-342.
Park Eun-Kyung et al: "Astaxanthin production by Haematococcus pluvialis under various light intensities and wavelengths", Journal of Microbiology and Biotechnology, Korean Society for Applied Microbiology, Seoul, KR, vol. 11, No. 6, Dec. 2001 (Dec. 2001), pp. 1024-1030.
J.M. Pickett: "Effects of Flashes of Red or Blue Light on the Composition of Starved Chlorella pyrenoidosa", Plant Physiology., vol. 47, No. 2, Feb. 1971 (Feb. 1971), pp. 226-229.
R. Schmid: "Photosynthesis of Ectocarpus siliculosus in red light and after pulses of blue light at high pH—evidence for bicarbonate uptake", Plant Cell and Environment, vol. 21, No. 5, May 1998 (May 1998), pp. 523-529.
Communication dated Aug. 16, 2016, from the European Patent Office in counterpart European Application No. 14746315.2.
Communication dated Jul. 13, 2016, from the European Patent Office in counterpart European Application No. 14745336.9.

\* cited by examiner

METHOD OF PROMOTING GROWTH OF GREEN ALGAE

CROSS REFERENCE TO RELATED APPLICATIONS

This application is a National Stage of International Application No. PCT/JP2014/052531, filed Feb. 4, 2014, claiming priority based on Japanese Patent Application No. 2013-019975, filed Feb. 4, 2013, the contents of all of which are incorporated herein by reference in their entirety.

TECHNICAL FIELD

The present invention relates to a method of promoting the growth of green algae, and particularly to a method of promoting the growth of green algae which promotes the growth of the green algae which is in a state of being a swarm cell by irradiating the green algae that accumulate astaxanthin, with artificial light.

Priority is claimed on Japanese Patent Application No. 2013-019975, filed Feb. 4, 2013, the content of which is incorporated herein by reference.

BACKGROUND ART

It is known that astaxanthin is a kind of red carotenoid and has a strong antioxidant effect.

PTL 1 discloses a method of producing a green alga that produces astaxanthin and a method of producing a green alga containing astaxanthin in a high concentration by irradiating a green alga, the cell of which is changed to a cyst cell, with light under certain conditions.

Green algae belonging to the genus *Haematococcus* have been known as green algae which accumulate astaxanthin. It has been known that the *Haematococcus* exists in a state of being grown as a green swarm cell under an appropriate culture and light irradiation conditions and in a state in which the swarm cell is changed to the cyst cell due to stress such as a light environment or nutrition deficiency and a significant amount of astaxanthin is accumulated in the cell.

It is commercially useful to industrially culture a large amount of green algae as raw materials for health food products, pharmaceutical products, or the like. Moreover, a method of increasing the accumulation of astaxanthin in the cyst cell as shown in PTL 1 has been studied.

On the other hand, there is a need to improve the productivity by promoting the growth of the green algae and by shortening the culture period. In this manner, in order to shorten the period required for obtaining a large amount of cells, it is useful to promote the growth of the green algae which is in a state of being the swarm cell, which is a cell prior to being changed to the cyst cell, and to produce a cell in high density in a short period of time. However, the method of promoting the growth of the green algae which is in a state of being the swarm cell is not known.

In addition, a method of growing an organism by promoting photosynthesis using artificial light is known.

For example, NPL 1 discloses an effect of irradiation with red LED light and blue LED light, on the growth of the *Haematococcus*.

In addition, PTL 2 discloses a light source for cultivating a plant or the like by simultaneously or alternately turning on the blue LED light and the red LED light.

CITATION LIST

Patent Literature

[PTL 1] Japanese Unexamined Patent Application, First Publication No. 2007-097584
[PTL 2] Japanese Unexamined Patent Application, First Publication No. H08-103167

Non-Patent Literature

[NPL 1] Katsuda, T., et al., Enzyme and Microbial Technology 35 (2004) 81-86

SUMMARY OF INVENTION

Technical Problem

None of the above-described literature discloses the method of promoting the growth of the green algae which is in a state of being the swarm cell in a liquid medium and culturing the cell in high density. Moreover, such a method is not known.

Therefore, the present invention has been made in consideration of the above-described circumstances, and an object of the present invention is to provide a growth promoting method for improving the productivity by promoting the growth of the green algae which is in a state of being the swarm cell and by shortening the culture period, in order to industrially culture a large amount of the green algae that accumulate astaxanthin.

Solution to Problem

The present inventors have conducted extensive studies on the effect of promoting the growth of the green algae by radiating an artificial light. As a result, they have found that, surprisingly, the swarm cell grows in high density in a short period of time while maintaining a green stage (a state in which the color of a culture solution is green or brown during the culturing of the green algae) if red illumination light is intermittently radiated while continuously radiating the blue illumination light.

The present invention is as follows.

[1] A method of promoting growth of green algae which promotes the growth of the green algae which is in a state of being a green swarm cell by irradiating the green algae that accumulate astaxanthin with an artificial light,
in which the green algae are grown in a liquid medium while maintaining a state in which the color of a culture solution of the green algae is green or brown by intermittently radiating a red illumination light while continuously radiating a blue illumination light.

[2] The method of promoting growth of green algae according to the above-described [1], in which the green algae accumulating astaxanthin are unicellular green algae belonging to the genus *Haematococcus*.

[3] The method of promoting growth of green algae according to the above-described [2], in which the unicellular green algae belonging to the genus *Haematococcus* are *Haematococcus pluvialis* (*H. pluvialis*) or *Haematococcus lacustris* (*H. lacustris*).

[4] The method of promoting growth of green algae according to any one of the above-described [1] to [3], in which a wavelength of the red illumination light is 570 nm to 730 nm and a central wavelength is 645 nm to 680 nm.

[5] The method of promoting growth of green algae according to any one of the above-described [1] to [4], in which a wavelength of the blue illumination light is 400 nm to 515 nm and a central wavelength is 440 nm to 460 nm.

[6] The method of promoting growth of green algae according to any one of the above-described [1] to [5], in which a light source of the red illumination light is an LED.

[7] The method of promoting growth of green algae according to any one of the above-described [1] to [6], in which a light source of the blue illumination light is an LED.

[8] The method of promoting the growth of green algae according to any one of the above-described [1] to [7], in which the light amount of the red illumination light and the blue illumination light is 10 $\mu mol/m^2/s$ to 100 $\mu mol/m^2/s$ at photosynthetic photon flux density in a light irradiation surface of the culture solution.

[9] The method of promoting the growth of green algae according to any one of the above-described [1] to [8], in which the irradiation period of the red illumination light is 1 hour to 24 hours per each time and the non-irradiation period thereof is 1 hour to 24 hours per each time.

[10] The method of promoting the growth of green algae according to any one of the above-described [1] to [9], in which the period of a cycle of intermittent irradiation performed once for each of the irradiation and non-irradiation with the red illumination light is 2 hours to 24 hours.

Advantageous Effects of Invention

According to the present invention, in a method of promoting the growth of green algae that accumulate astaxanthin, a simple and excellent growth promoting method, by which it is possible to shorten the culture period and to improve productivity by promoting the growth which is in a state of being a swarm cell, is provided.

In addition, according to the growth promoting method of the present invention, it is possible to promote the growth of the green algae which is in a state of being the swarm cell and to produce a cell in high density in a short period of time. Moreover, it is possible to obtain a large amount of green algae (to grow the swarm cell) using the growth promoting method of the present invention, and then, to efficiently produce a large amount of astaxanthin by transferring the obtained green algae to the cyst cell.

DESCRIPTION OF EMBODIMENTS

Hereinafter, preferred embodiments of the present invention will be described. The embodiments described below are examples of representative embodiments of the present invention and the present invention is not limited thereto. Therefore, the scope of the present invention is not interpreted narrowly.

The method of promoting the growth of green algae according to the present invention is a method of promoting the growth of a swarm cell in a liquid medium while maintaining a green stage (a state in which the color of a culture solution is green or brown during the culturing of the green algae) of green algae by intermittently radiating a red illumination light while continuously radiating a blue illumination light with respect to the green algae that accumulate astaxanthin.

Here, the "continuous radiation" refers to radiation over the whole period (culture period) of promoting the growth of green algae and the "intermittent radiation" refers to repetition of a cycle of irradiation and non-irradiation performed such that light is radiated for a certain period of time during the culture period and is not subsequently radiated for a certain period of time, and then, light is further radiated for a certain period of time and is not subsequently radiated for a certain period time.

(Wavelength)

An example of the red illumination light used in the present invention includes light having a wavelength of 570 nm to 730 nm, and light having a wavelength of 620 nm to 730 nm is preferably used. In addition, red illumination light, which has a wavelength of 645 nm to 680 nm as a central wavelength, is more preferably used and red illumination light having a central wavelength of 660 nm is still more preferable.

An example of the blue illumination light used in the present invention includes light having a wavelength of 400 nm to 515 nm.

In addition, blue illumination light having a central wavelength of 440 nm to 460 nm is preferably used and blue illumination light having a central wavelength of 445 nm to 450 nm is more preferable.

The red illumination light and the blue illumination light can have a predetermined wavelength region by having the above-described wavelengths as central wavelengths. Examples of the wavelength regions include, for the blue illumination light, 450 nm±30 nm, preferably 450 nm±20 nm, and more preferably 450 nm±10 nm, and for the red illumination light, 660 nm±30 nm, preferably 660 nm±20 nm, and more preferably 660 nm±10 nm.

(Light Amount)

The light amounts of the red irradiation light and the blue irradiation light are not particularly limited as long as the light amounts are within a range where it is suitable to grow green algae accumulating astaxanthin. For example, respective photosynthetic photon flux densities (PPFD) in the vicinity of a light irradiation surface of the culture solution are 5 $\mu mol/m^2/s$ to 200 $\mu mol/m^2/s$, preferably 10 $\mu mol/m^2/s$ to 100 $\mu mol/m^2/s$, and more preferably 20 $\mu mol/m^2/s$ to 70 $\mu mol/m^2/s$. The light amounts of the red irradiation light and the blue irradiation light may be the same as or different from each other.

The "light irradiation surface" refers to a place (a place close to the light irradiation surface without limitation) which is close to the culture solution and is not being limited to a place next to the culture solution, while it is difficult to strictly define the "light irradiation surface" from the size of equipment of measuring PPFD or the shape of a culture container.

In addition, the light amount ratios of the red irradiation light and the blue irradiation light are not limited as long as the effect of the present invention can be obtained. For example, it is possible to set the range of the light amount ratio of "red:blue" to 1:20 to 20:1 and it is possible to arbitrarily set the range thereof to 1:1, 5:3, 2:1, 3:1, 4:1, 10:1, 20:1, and the like. Among these, the light amount ratio of "red:blue" is preferably within a range of 1:1 to 10:1, more preferably within a range of 3:2 to 7:1, and still more preferably within a range of 5:3 to 3:1.

(Irradiation Period and Non-Irradiation Period)

The irradiation period and the non-irradiation period of the red irradiation light can be arbitrarily set in so far as the effect of the present invention is exhibited. A preferred irradiation period is 1 hour to 24 hours per each time, more preferably 1 hour to 18 hours, and still more preferably 1 hour to 12 hours. The irradiation period may be constant throughout the whole culture period and may be extended or shortened for each irradiation.

A preferred non-irradiation period is 1 hour to 24 hours per each time, more preferably 6 hours to 23 hours, and still more preferably 12 hours to 23 hours. The non-irradiation period may be constant throughout the whole culture period and may be extended or shortened for each irradiation.

Here, each time of the irradiation and the non-irradiation is set to a cycle of the intermittent irradiation. The period of a cycle can be arbitrarily set as a total of the irradiation period and the non-irradiation period. A preferred period of a cycle is 2 hours to 48 hours and more preferably 2 hours to 24 hours. The process may start from either the irradiation or the non-irradiation at the time of starting the culturing and may finish with either the irradiation or the non-irradiation.

An example of a preferred mode includes conditions in which light amount of the red irradiation light is 62.5 $\mu mol/m^2/s$, light amount of the blue irradiation light is 18.8 $\mu mol/m^2/s$, the irradiation period of the red irradiation light is 12 hours, and the non-irradiation period thereof is 12 hours, being constant throughout the culture period. At this time, the light amount ratio (red illumination light:blue illumination light) per 24 hours is 5:3.

(Irradiation Device)

Any device for irradiating the red irradiation light and the blue irradiation light used in the present invention can be used regardless of the shape of the device or the type of the light source as long as it is possible to perform a process of continuously radiating the blue irradiation and a process of intermittently radiating the red irradiation light in the present invention. The device includes a light irradiation unit that irradiates the green algae with the red illumination light and the blue illumination light and a control unit that performs the intermittent irradiation with the red illumination light by controlling the light irradiation unit.

A light source for radiating red light and/or blue light is included in the light irradiation unit. It is possible to use a conventionally known light source for a light source of the red light and the blue light. It is preferable that a photosemiconductor element such as a light emitting diode (LED) or a laser diode (LD) that radiates light, in which it is easy to select the wavelength and in which the percentage of light energy in an effective wavelength region is large, be used for a light source.

The photo-semiconductor element is small in size and has a long service life. Moreover, the photo-semiconductor element has good energy efficiency as it emits at a specific wavelength depending on the material and there is no unnecessary heat radiation. Furthermore, the photo-semiconductor element hardly disturbs a cell even if close irradiation is performed on green algae. For this reason, it is possible to perform the culturing at low electric power cost while saving space compared to other light sources using the photo-semiconductor element for a light source.

It is possible to use an SMD line light source, in which an SMD (two chips surface mount device) mounted with a combination of a red light semiconductor element and a blue light semiconductor element is arranged in a linear shape; a monochromatic line light source or a monochromatic panel light source, in which either the red light semiconductor element or the blue light semiconductor element is arranged in a linear, tubular, or planar shape; and the like, for a light source.

Examples of LEDs that radiate light in the above-described wavelength region include an ALGaOnP light emitting diode (GaP substrate, 660 nm of a red wavelength) which is available as a product number of HRP-350F from Showa Denko K.K. or the like for a red LED; and a light emitting diode having a product number of GM2LR450G of Showa Denko K.K. or the like for a blue LED.

Examples of light sources other than the light emitting diode include a straight-tube type or a compact type fluorescent lamp and an electric bulb-type fluorescent lamp, a high-pressure discharge lamp, a metal halide lamp, and a laser diode. An optical filter may be used in order to selectively use the light in the above-described wavelength region by combining the light sources.

The control unit maintains the light amounts and/or the irradiation periods of the red illumination light and the blue illumination light, which are radiated from the light irradiation unit, to be predetermined values or changes the light amounts and the irradiation periods thereof to predetermined light amounts and irradiation periods.

The control unit can be configured by using a general computer. For example, in a case where an LED is used for a light source, the size of a drive current of an LED is adjusted based on a control pattern which is previously held and stored in a memory or a hard disk, and the light amounts and/or the irradiation periods of the red illumination light and the blue illumination light is changed. In addition, the control unit switches and drives a plurality of LEDs radiating light beams in different wavelength regions based on the control pattern and changes the wavelength region of the radiated light.

(Algae)

Green algae used in the present invention can be used without particular limitation as long as the green algae accumulate astaxanthin. For example, unicellular green algae belonging to the genus *Haematococcus* are preferably used.

Examples of preferred green algae include *Haematococcus pluvialis* (*H. pluvialis*), *Haematococcus lacustris* (*H. lacustris*), *Haematococcus capensis* (*H. capensis*), *Haematococcus droebakensi* (*H. droebakensi*), and *Haematococcus zimbabwiensis* (*H. zimbabwiensis*).

Examples of *Haematococcus pluvialis* (*H. pluvialis*) include a UTEX 2505 strain and a K 0084 strain.

Examples of *Haematococcus lacustris* (*H. lacustris*) include an NIES 144 strain, an ATCC 30402 strain, an ACTT 30453 strain, an IAM C-392 strain, an IAM C-393 strain, an IAM C-394 strain, an IAM C-339 strain, a UTEX 16 strain, and a UTEX 294 strain.

An example of *Haematococcus capensis* (*H. capensis*) includes a UTEX LB 1023 strain.

An example of *Haematococcus droebakensi* (*H. droebakensi*) includes a UTEX 55 strain.

An example of *Haematococcus zimbabwiensis* (*H. zimbabwiensis*) includes UTEX LB 1758 strain.

Among these, *Haematococcus pluvialis* (*H. pluvialis*) is preferably used.

(Green Stage)

A green stage in the present invention indicates a state in which the color of a culture solution is green or brown during the culturing of green algae and corresponds to a state in which a cell within a medium grows as a green swarm cell under an appropriate culture and light irradiation conditions.

In contrast, a state, in which the swarm cell is changed to the cyst cell due to stress such as a light environment or nutritional deficiency and the color of the culture solution is changed to red by accumulating a significant amount of astaxanthin in the cell, is called a red stage.

The appropriate culture and light irradiation conditions indicates that red illumination light and blue illumination light having a wavelength described in the specification are radiated using an irradiation device at a light amount for an irradiation period and a non-irradiation period described in the specification, and the culturing is performed under the culture condition using the algae, the medium, and the culture device described in the specification.

At the end of the green stage while being transferred to the red stage from the green stage, a green cell (cell which maintains a state of the swarm cell) and a red cell (cell which is changed to the cyst cell) are mixed and the color of the culture solution is changed to brown. Finally, the swarm cell disappears and the stage is transferred to the red stage in which a significant amount of astaxanthin is accumulated.

In order to produce a large amount of astaxanthin, it is preferable to transfer the stage to the red stage after promoting the growth of the green algae which is in a state of being the swarm cell and producing a cell in high density in a short period of time, while maintaining the green stage, that is, a state immediately before the color of culture solution becomes red (a state in which there is a swam cell in the medium and which includes not only a state where the color of the culture solution is green but also a state where the color of the culture solution is brown) as possible. In the growth promoting method of the present invention, it is possible to grow a cell in high density in a short period of time by realizing the above.

(Medium)

A liquid medium used in the culturing of green algae is not particularly limited. In general, it is possible to preferably use a medium containing nitrogen, trace metal inorganic salts (for example, phosphorus, potassium, magnesium, and iron), and vitamins (for example, thiamin) which are required for proliferation. For example, it is possible to use media such as an AF-6 medium, a BG-11 medium, a C medium, an MBM medium, an MDM medium, and a VT medium (the medium compositions are disclosed in the list of media in the homepage of Incorporated Administrative Agency National Institute of Health Sciences), modified media thereof, and the like. The media can be appropriately selected in accordance with the types of green algae or the purpose of culturing. For example, for the purpose of growing the green alga belonging to the genus *Haematococcus*, it is preferable to use the *C medium* or the BG-11 medium and modified media thereof. Components such as a carbon source and a nitrogen source may be appropriately added in addition to the above-described compositions.

(Culture Device)

The shape or the size of the culture device of the green algae is not particularly limited as long as the device can supply carbon dioxide and can radiate light. For example, in a case where the culturing is performed in a laboratory, it is possible to use a flat culture bottle, a conical flask, a flat-bottom flask, or the like. In a case where the culturing is performed at a pilot scale or an industrial production scale, it is possible to use a culture tank, which is provided with a device that can irradiate a transparent container made of glass or plastic with light from the outside or the inside thereof, or a culture tank, which is provided with a device that can irradiate the inside of a metallic container with light from the inside thereof. As such a culture tank, for example, a jar-type culture tank, a tube-type culture tank, an air-dome type culture tank, and a hollow cylindrical culture tank are used. In addition, in any case, an airtight container is preferably used. The tanks may be installed with a stirring machine as necessary.

(Culture Condition)

The culture condition is not particularly limited. The temperature, the pH, and the like which are generally used in the culturing of the green algae can be used. The temperature for culturing the green algae is controlled to be constant, for example, 15° C. to 35° C., and preferably 20° C. to 25° C. The pH of the culture solution is held between 4 and 10, preferably between 5 and 9, and more preferably between 6 and 8.

For the purpose of supplying the carbon source and controlling the pH, it is preferable to supply carbon dioxide. In general, mixed air containing carbon dioxide at a concentration of 1 v/v % to 10 v/v % is supplied to a medium or to the upper space of the culture tank. For example, the mixed air is supplied by being continuously circulated so as to be 0.2 vvm to 2 vvm. Alternatively, the carbon dioxide may be intermittently supplied by substituting the upper space of the culture tank with the above-described mixed air and sealing it, and then, repeating the substituting and the sealing. It is preferable that the concentration of the carbon dioxide be appropriately changed in accordance with the growth of the green algae or that the circulation amount be changed. As an example of a preferred culture condition, culturing is performed while supplying an appropriate circulation amount by changing the circulation amount so as to maintain the pH 7 in accordance with the growth of the green algae, by continuously circulating the mixed air containing carbon dioxide at a concentration of 5 v/v % so that the mixed air becomes 1 vvm, in a state where the cells of the green algae are gently stirred at a temperature of 20° C. and at the pH of 7 so as to evenly radiate light.

(Measurement of Amount of Algal Body)

It is possible to measure the growth state of the green algae using a known method such as measurement of absorbance of culture solution, fluorescence measurement, measurement using a hemocytometer, Coulter Counter, and dry weight measurement. Among these, the absorbance measurement at 560 nm, the measurement using hemocytometer, and the dry weight measurement are preferably performed.

EXAMPLES

Hereinafter, the effect of the present invention becomes clearer by the examples. The present invention is not limited to the following examples and can be implemented through appropriate modification within the scope not departing the gist of the present invention.

In the present examples, the present invention is described using examples using a *Haematococcus lacustris* NIES-144 strain. However, the present invention is not limited to the examples.

Example 1

Preparation of Green Alga

A modified medium of a BG-11 medium was prepared. The medium composition is shown in Table 1.

TABLE 1

| Composition | g/L |
| --- | --- |
| $NaNO_3$ | 0.45 |
| $K_2HPO_4 \cdot 3H_2O$ | 0.04 |
| $MgSO_4 \cdot 7H_2O$ | 0.075 |
| $CaCl_2 \cdot 2H_2O$ | 0.036 |
| Citric Acid (anhydrous) | 0.006 |
| Ammonium iron(III) cirate | 0.006 |
| EDTA·2Na | 0.001 |
| $Na_2CO_3$ | 0.02 |

TABLE 1-continued

| Composition | g/L |
| --- | --- |
| $H_3BO_4$ | 0.00181 |
| $MnCl_2 \cdot 4H_2O$ | 0.00022 |
| $ZnSO_4 \cdot 7H_2O$ | 0.00008 |
| $Na_2MoO_4$ | 0.000021 |
| $CuSO_4 \cdot 5H_2O$ | 0.079 |
| $Co(NO_3)_2 \cdot 6H_2O$ | 0.049 |

20 ml of a medium was input to a culture flask with a 50 ml capacity and a *Haematococcus lacustris* NIES-144 strain was inoculated. Photosynthesis-effective photon density (PPED) was adjusted to 30 μmol/m²/s on the irradiation surface of the culture flask using a light quantum meter (manufactured by System Instruments Co., Ltd.) and using a white fluorescent lamp for a light source; light irradiation was intermittently performed on the medium for 12 hours for an irradiation period and 12 hours for a non-irradiation period; the culture is performed for 14 days at a temperature of 20° C.; and a culture solution having a cell density of 2×10⁵ cell/ml was prepared.

(Main Culture)

20 ml of the same medium was input to a conical flask with a 100 ml capacity and 2 ml of the above-described culture solution was inoculated. The PPED was adjusted to 62.5 μmol/m²/s for red light and 18.8 μmol/m²/s for blue light on the irradiation surface of the culture solution using a light quantum meter and using 3 in 1 LED illumination (manufactured by NKsystem, wavelength: 660 nm for red light, 520 nm for green light, and 450 nm for blue light) for a light source; the medium was intermittently and repeatedly irradiated with the red illumination light having an irradiation period for 12 hours and a non-irradiation period for 12 hours while being continuously irradiated with the blue illumination light; and the culture was performed for 6 days at a temperature of 20° C. and a pH of 7. At this time, the light amount ratio of the red irradiation light to the blue irradiation light per 24 hours was 5:3.

While supplying carbon dioxide, gas containing carbon dioxide at a concentration of 7 v/v % to 10 v/v % was ventilated to a head space of the flask through a sterilization filter and the head space was sufficiently substituted with the gas, and then, the head space was sealed with a butyl rubber plug. Each time when the plug was released at the time of sampling, the head space was substituted with the gas through the same procedure.

During the culturing, the concentration of the carbon dioxide was adjusted so that the pH of the medium became 7. Specifically, the concentration of the carbon dioxide to be supplied was adjusted so as to be 7 v/v % from day 0 to day 4 and 10 v/v % after day 4.

The absorbance at 560 nm (A560) and the swarm cell ratio were measured by appropriately performing sampling during the culturing. The swarm cell ratio in the cell was calculated using the hemocytometer. In addition, the color of the culture solution was observed.

Example 2

The culturing was performed similarly to Example 1 except that the light irradiation condition was adjusted so as to be 75 μmol/m²/s for red light and 12.5 μmol/m²/s for blue light. At this time, the light amount ratio of the red irradiation light to the blue irradiation light per 24 hours was 3:1.

Example 3

The culturing was performed similarly to Example 1 except that the light irradiation condition was adjusted so as to be 87.5 μmol/m²/s for red light and 6.3 μmol/m²/s for blue light. At this time, the light amount ratio of the red irradiation light to the blue irradiation light per 24 hours was 7:1.

Comparative Example 1

The culturing was performed as the same as that in Example 1 except that the light irradiation condition was adjusted so as to be 31.3 μmol/m²/s for red light and 18.8 μmol/m²/s for blue light and the medium was simultaneously and continuously irradiated with the red irradiation light and the blue irradiation light. At this time, the light amount ratio of the red irradiation light to the blue irradiation light per 24 hours was 5:3.

Comparative Example 2

The culturing was performed as the same as that in Example 1 except that the light irradiation condition was adjusted so as to be 50 μmol/m²/s using a white fluorescent lamp for a light source and the medium was continuously irradiated.

Comparative Example 3

The culturing was performed similarly to Example 1 except that the light irradiation condition was adjusted so as to be 37.5 μmol/m²/s for red light and 12.5 μmol/m²/s for blue light, the medium was simultaneously and continuously irradiated with the red irradiation light and the blue irradiation light, and the main culturing was performed for 6 days. At this time, the light amount ratio of the red irradiation light to the blue irradiation light per 24 hours was 3:1.

Comparative Example 4

The culturing was performed similarly to Example 1 except that the light irradiation condition was adjusted so as to be 43.7 μmol/m²/s for red light and 6.3 μmol/m²/s for blue light, the medium was simultaneously and continuously irradiated with the red irradiation light and the blue irradiation light, and the main culturing was performed for 6 days. At this time, the light amount ratio of the red irradiation light to the blue irradiation light per 24 hours was 7:1.

The result of A560 of Example 1 and Comparative Examples 1 to 4, at days 4 and 6 is shown as the following.

In Example 1, A560 was high and the growth was promoted compared to Comparative Examples 1 and 2. In Example 1, the swarm cell ratio was 70% and the color of the culture solution was green, and the green stage was maintained.

In Examples 2 and 3, A560 and the cell density were high and the growth was promoted compared to Comparative Examples 3 and 4. In all of Examples 2 and 3 and Comparative Examples 3 and 4, the color of the culture solution was green at day 6, the swarm cell ratio was greater than or equal to 70%, and the green stage was maintained.

In contrast, in Comparative Examples 1 and 2, the color of the culture solution became red at day 6, and therefore, it was impossible to maintain the green stage.

In addition, in Comparative Examples 3 and 4, while the color of the culture solution was maintained to be green at day 6, the cells were coagulated causing precipitation.

TABLE 2

| | Green algae | Medium | Culture device | Main culture conditions ||||
|---|---|---|---|---|---|---|---|
| | | | | Temperature (° C.) | pH | Period (day) | Light source |
| Example 1 | Haematococcus lacustris N1ES-144 strain | Modified medium of BG-11 medium | 100 ml conical flask | 20 | 7 | 6 | 3 in LED illumination |
| Example 2 | Haematococcus lacustris N1ES-144 strain | Modified medium of BG-11 medium | 100 ml conical flask | 20 | 7 | 6 | 3 in LED illumination |
| Example 3 | Haematococcus lacustris N1ES-144 strain | Modified medium of BG-11 medium | 100 ml conical flask | 20 | 7 | 6 | 3 in LED illumination |
| Comparative Example 1 | Haematococcus lacustris N1ES-144 strain | Modified medium of BG-11 medium | 100 ml conical flask | 20 | 7 | 6 | 3 in LED illumination |
| Comparative Example 2 | Haematococcus lacustris N1ES-144 strain | Modified medium of BG-11 medium | 100 ml conical flask | 20 | 7 | 6 | 3 in LED illumination |
| Comparative Example 3 | Haematococcus lacustris N1ES-144 strain | Modified medium of BG-11 medium | 100 ml conical flask | 20 | 7 | 6 | 3 in LED illumination |
| Comparative Example 4 | Haematococcus lacustris N1ES-144 strain | Modified medium of BG-11 medium | 100 ml conical flask | 20 | 7 | 6 | 3 in LED illumination |

| | Light irradiation conditions ||||||| A560 || swarm cell ratio (%) |
|---|---|---|---|---|---|---|---|---|---|---|
| | Light quantum density || Light irradiation conditions || Light amount ratio || | | |
| | Red (660 nm of wavelength) $\mu mol/m^2/s$ | Blue (450 nm of wavelength) $\mu mol/m^2/s$ | Red (hour/day) | Blue (hour/day) | Red | Blue | Day 4 | Day 6 | Day 6 |
| Example 1 | 62.5 | 18.8 | Irradiation: 12 Non-irradiation: 12 | Continuous irradiation | 5 | 3 | 0.26 | 0.66 | 70 |
| Example 2 | 75 | 12.5 | Irradiation: 12 Non-irradiation: 12 | Continuous irradiation | 3 | 1 | — | 0.61 | 80 |
| Example 3 | 87.5 | 6.3 | Irradiation: 12 Non-irradiation: 12 | Continuous irradiation | 7 | 1 | — | 0.6 | 80 |
| Comparative Example 1 | 31.3 | 18.8 | Simultaneous and continuous irradiation || 5 | 3 | 0.23 | 0.57 | — |
| Comparative Example 2 | White fluorescent lamp: 50 || — | — | — | — | 0.16 | 0.39 | — |
| Comparative Example 3 | 37.5 | 12.5 | Simultaneous and continuous irradiation || 3 | 1 | — | 0.53 | 70 |
| Comparative Example 4 | 43.7 | 6.3 | Simultaneous and continuous irradiation || 7 | 1 | — | 0.52 | 70 |

The invention claimed is:

1. A method of promoting growth of green algae which promotes the growth of the green algae which is in a state of being a green swarm cell by irradiating the green algae that accumulate astaxanthin with an artificial light,
wherein the green algae are grown in a liquid medium while maintaining a state in which the color of a culture solution of the green algae is green or brown by intermittently radiating a red illumination light while continuously radiating a blue illumination light,
a light amount ratio of the red illumination light and the blue illumination light is within a range of 1:1 to 10:1, and
the irradiation period of the red illumination light is 1 hour to 24 hours per each time and the non-irradiation period thereof is 1 hour to 24 hours per each time.

2. The method of promoting growth of green algae according to claim 1, wherein the green algae accumulating astaxanthin are unicellular green algae belonging to the genus *Haematococcus*.

3. The method of promoting growth of green algae according to claim 2, wherein the unicellular green algae belonging to the genus *Haematococcus* are *Haematococcus pluvialis* (*H. pluvialis*) or *Haematococcus lacustris* (*H. lacustris*).

4. The method of promoting growth of green algae according to claim 1, wherein a wavelength of the red illumination light is 570 nm to 730 nm and a central wavelength is 645 nm to 680 nm.

5. The method of promoting growth of green algae according to claim 1, wherein a wavelength of the blue illumination light is 400 nm to 515 nm and a central wavelength is 440 nm to 460 nm.

6. The method of promoting growth of green algae according to claim 1, wherein a light source of the red illumination light is an LED.

7. The method of promoting growth of green algae according to claim 1, wherein a light source of the blue illumination light is an LED.

8. The method of promoting growth of green algae according to claim 1, wherein the light amount of the red illumination light and the blue illumination light is 10 $\mu mol/m^2/s$ to 100 $\mu mol/m^2/s$ at photosynthetic photon flux density in a light irradiation surface of the culture solution.

9. The method of promoting growth of green algae according to claim 1, wherein the period of a cycle of intermittent irradiation performed once for each of the irradiation and the non-irradiation with the red illumination light is 2 hours to 24 hours.

* * * * *